(12) United States Patent
Taghibiglou et al.

(10) Patent No.: US 11,117,939 B2
(45) Date of Patent: Sep. 14, 2021

(54) POLYPEPTIDES AND ANTIBODIES TO TREAT SKIN CONDITIONS ASSOCIATED WITH OVERPRODUCTION OF SEBUM

(71) Applicants: Changiz Taghibiglou, Saskatoon (CA); Yu Tian Wang, Vancouver (CA)

(72) Inventors: Changiz Taghibiglou, Saskatoon (CA); Yu Tian Wang, Vancouver (CA)

(73) Assignee: University of Sasketchewan, Saskatoon (CA)

( * ) Notice: Subject to any disclaimer, the term of this patent is extended or adjusted under 35 U.S.C. 154(b) by 283 days.

(21) Appl. No.: 15/576,747

(22) PCT Filed: May 27, 2016

(86) PCT No.: PCT/CA2016/050605
§ 371 (c)(1),
(2) Date: Nov. 24, 2017

(87) PCT Pub. No.: WO2016/191864
PCT Pub. Date: Dec. 8, 2016

(65) Prior Publication Data
US 2018/0305419 A1 Oct. 25, 2018

Related U.S. Application Data

(60) Provisional application No. 62/168,374, filed on May 29, 2015.

(51) Int. Cl.
| | |
|---|---|
| C07K 14/47 | (2006.01) |
| A61P 17/10 | (2006.01) |
| A61P 17/08 | (2006.01) |
| A61K 9/00 | (2006.01) |
| A61K 38/17 | (2006.01) |
| C07K 16/18 | (2006.01) |
| C07K 14/705 | (2006.01) |
| A61K 39/395 | (2006.01) |
| A61Q 19/00 | (2006.01) |
| A61K 8/64 | (2006.01) |
| C12N 5/071 | (2010.01) |

(52) U.S. Cl.
CPC .............. *C07K 14/47* (2013.01); *A61K 8/64* (2013.01); *A61K 9/0014* (2013.01); *A61K 38/1709* (2013.01); *A61K 39/395* (2013.01); *A61P 17/08* (2018.01); *A61P 17/10* (2018.01); *A61Q 19/008* (2013.01); *C07K 14/705* (2013.01); *C07K 16/18* (2013.01); *C12N 5/0625* (2013.01); *C07K 2319/10* (2013.01); *C12N 2501/998* (2013.01)

(58) Field of Classification Search
None
See application file for complete search history.

(56) References Cited

U.S. PATENT DOCUMENTS

2010/0215634 A1  8/2010  Tennenbaum et al.

FOREIGN PATENT DOCUMENTS

| KR | 10-2014-0145499 | * 12/2014 |
| WO | 2009/121176 | 10/2009 |
| WO | WO 2011/129399 | * 10/2011 |

OTHER PUBLICATIONS

Machine translation of KR 10-2014-0145499 (published Dec. 2014).*
Zhou et al.,Lipids in Health and Disease 2012, 11:156, http://www.lipidworld.com/content/11/1/156.*
Smith et al., J Invest Dermatol. May 2008; 128(5): 1286-1293. doi:10.1038/sj.jid.5701155.*
Machine translation of WO 2011/129399 (published Oct. 2011).*
Piewig et al., Acne and Rosacea, Springer-Verlag Berlin Heidelberg 2000, pp. 254-267.*
Oble et al., Journal of Investigative Dermatology, 124:151-159, 2005.*
Borda et al., J Clin Investig Dermatol. Dec. 2015; 3(2):1-22.*
Changiz Taghibiglou et al: Sterol regulatory element binding protein-1 (SREBP1) activation in motor neurons in excitotoxicity and amyotrophic lateral sclerosis (ALS): Indip, a potential therapeutic peptide, Biochemical and Biophysical Research Communicaitons, vol. 413, No. 2, pp. 159-163, XP028391497, ISSN: 0006-291X, COI: 10.1016/J.BBRC.2011.08.011.
Evers et al., Hair Growth Defects in Insig-deficient Mice Caused by Cholesterol Precursor Accumulation and Reversed by Simvastatin, J. Invest Dermator 130:1237-1248, Jan. 21, 2010.
Rosignoli et al., Involvement of SREBP Pathway in the Mode of Action and Androngens in Sebaceous Glands in Vivo, Exp. Dermatol, 12:480-489, 2003 ISSN: 0906-6705.

* cited by examiner

*Primary Examiner* — Marianne P Allen
(74) *Attorney, Agent, or Firm* — Michael R Williams; Ryan W Dupius; Ade & Company Inc.

(57) ABSTRACT

The present application provides compositions, methods, and uses of polypeptide or antibody inhibitors of insig-1 ubiquitination for preventing or treating skin diseases or conditions associated with overproduction of sebum, such as acne and seborrhea.

10 Claims, 3 Drawing Sheets
Specification includes a Sequence Listing.

SEQUENCE LISTING

<160> NUMBER OF SEQ ID NOS: 21

<210> SEQ ID NO 1
<211> LENGTH: 10
<212> TYPE: PRT
<213> ORGANISM: Homo Sapiens

<400> SEQUENCE: 1

Gly Glu Pro His Lys Phe Lys Arg Glu Trp
1               5                   10

<210> SEQ ID NO 2
<211> LENGTH: 21
<212> TYPE: PRT

```
<213> ORGANISM: artificial sequence
<220> FEATURE:
<223> OTHER INFORMATION: Synthetic Peptide
<220> FEATURE:
<221> NAME/KEY: MISC_FEATURE
<222> LOCATION: (1)..(11)
<223> OTHER INFORMATION: Tat
<220> FEATURE:
<221> NAME/KEY: MISC_FEATURE
<222> LOCATION: (12)..(21)
<223> OTHER INFORMATION: Insig-1

<400> SEQUENCE: 2

Tyr Gly Arg Lys Lys Arg Arg Gln Arg Arg Gly Glu Pro His Lys
1               5                   10                  15

Phe Lys Arg Glu Trp
            20

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(11)
<223> OTHER INFORMATION: Insig-1

<400> SEQUENCE: 3

Gly Gly Glu Pro His Lys Phe Lys Arg Glu Trp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(12)
<223> OTHER INFORMATION: Insig-1

<400> SEQUENCE: 4

Gly Gly Gly Glu Pro His Lys Phe Lys Arg Glu Trp
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(13)
<223> OTHER INFORMATION: Insig-1

<400> SEQUENCE: 5

Gly Gly Gly Gly Glu Pro His Lys Phe Lys Arg Glu Trp
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (5)..(14)
<223> OTHER INFORMATION: Insig-1

<400> SEQUENCE: 6

Gly Gly Gly Gly Gly Glu Pro His Lys Phe Lys Arg Glu Trp
1               5                   10

<210> SEQ ID NO 7
<211> LENGTH: 9
<212> TYPE: PRT
<213> ORGANISM: Homo Sapiens

<400> SEQUENCE: 7

Glu Pro His Lys Phe Lys Arg Glu Trp
1               5

<210> SEQ ID NO 8
<211> LENGTH: 9
<212> TYPE: PRT
<213> ORGANISM: Homo Sapiens

<400> SEQUENCE: 8

Gly Glu Pro His Lys Phe Lys Arg Glu
1               5

<210> SEQ ID NO 9
<211> LENGTH: 8
<212> TYPE: PRT
<213> ORGANISM: Homo Sapiens

<400> SEQUENCE: 9

Glu Pro His Lys Phe Lys Arg Glu
1               5

<210> SEQ ID NO 10
<211> LENGTH: 9
<212> TYPE: PRT
<213> ORGANISM: Homo Sapiens

<400> SEQUENCE: 10

Gly Glu Pro His Lys Phe Lys Arg Glu
1               5

<210> SEQ ID NO 11
<211> LENGTH: 8
<212> TYPE: PRT
<213> ORGANISM: Homo Sapiens

<400> SEQUENCE: 11

Glu Pro His Lys Phe Lys Arg Glu
1               5

<210> SEQ ID NO 12
<211> LENGTH: 7
<212> TYPE: PRT
<213> ORGANISM: Homo Sapiens

<400> SEQUENCE: 12

Pro His Lys Phe Lys Arg Glu
1               5

<210> SEQ ID NO 13
<211> LENGTH: 6
<212> TYPE: PRT
```

```
<213> ORGANISM: Artificial Sequence
<220> FEATURE:
<223> OTHER INFORMATION: Homo Sapiens

<400> SEQUENCE: 13

Pro His Lys Phe Lys Arg
1               5

<210> SEQ ID NO 14
<211> LENGTH: 6
<212> TYPE: PRT
<213> ORGANISM: Homo Sapiens

<400> SEQUENCE: 14

Pro His Lys Phe Lys Lys
1               5

<210> SEQ ID NO 15
<211> LENGTH: 9
<212> TYPE: PRT
<213> ORGANISM: Homo Sapiens

<400> SEQUENCE: 15

Asp Pro His Lys Phe Lys Arg Glu Trp
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(8)
<223> OTHER INFORMATION: Insig-1

<400> SEQUENCE: 16

Glu Pro His Lys Phe Lys Arg Glu Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(8)
<223> OTHER INFORMATION: Insig-1

<400> SEQUENCE: 17

Asp Pro His Lys Phe Lys Arg Glu Phe
1               5

<210> SEQ ID NO 18
<211> LENGTH: 9
<212> TYPE: PRT
<213> ORGANISM: artificial Sequence
<220> FEATURE:
<223> OTHER INFORMATION: Synthetic Peptide
<220> FEATURE:
<221> NAME/KEY: MISC_FEATURE
<222> LOCATION: (1)..(9)
<223> OTHER INFORMATION: Insig-1
<220> FEATURE:
<221> NAME/KEY: MISC_FEATURE
<222> LOCATION: (8)..(8)
```

```
<223> OTHER INFORMATION: Glu to Asp

<400> SEQUENCE: 18

Glu Pro His Lys Phe Lys Arg Asp Trp
1               5

<210> SEQ ID NO 19
<211> LENGTH: 8
<212> TYPE: PRT
<213> ORGANISM: Homo Sapiens

<400> SEQUENCE: 19

Glu Pro His Lys Phe Lys Arg Asp
1               5

<210> SEQ ID NO 20
<211> LENGTH: 7
<212> TYPE: PRT
<213> ORGANISM: Homo Sapiens

<400> SEQUENCE: 20

Pro His Lys Phe Lys Arg Asp
1               5

<210> SEQ ID NO 21
<211> LENGTH: 5
<212> TYPE: PRT
<213> ORGANISM: Homo Sapiens

<400> SEQUENCE: 21

His Lys Phe Lys Arg
1               5
```

POLYPEPTIDES AND ANTIBODIES TO TREAT SKIN CONDITIONS ASSOCIATED WITH OVERPRODUCTION OF SEBUM

CROSS-REFERENCE TO RELATED APPLICATIONS

This application claims the priority date benefit of U.S. provisional patent application No. 62/168,374 filed on May 29, 2015, the contents of which are hereby incorporated by reference.

FIELD

The present application relates generally to lipid metabolism, and more specifically to the use of lipid metabolism mediators to treat skin conditions.

BACKGROUND

Sterol regulatory element binding proteins (SREBPs) are endoplasmic reticulum (ER) membrane bound transcription factors best known for their role in activating genes required for cholesterol, fatty acid, triglyceride and phospholipid biosynthesis. SREBP-1 is mostly implicated in regulation of genes involved in fatty acid, phospholipid and triglyceride synthesis, while SREBP-2 is responsible for regulating genes in the cholesterol biosynthesis pathway (Goldstein et al. 2006). In the ER membrane, immature SREBPs exist in a tight association with SREBP cleavage activating protein (SCAP) (Nohturfft et al. 1998). SCAP determines the fate of SREBP based on cellular cholesterol levels or cellular stress. In the case of sterol depletion/cellular stress, SCAP interacts with a member of COPII coat proteins and escorts immature SREBPs (full-length) to the Golgi where they are proteolytically processed and N-terminal released as active (mature) transcription factors. When the cellular cholesterol level is high (or there is no cellular stress), SCAP binds to another ER membrane resident protein called Insig (there are two isoforms, Insig-1 and -2) (Flury et al. 2005) which retains the SREBP-SCAP complex in the ER membrane (Yang et al. 2002; Sun et al. 2005). In cholesterol-depleted cells, Insig-1 protein is rapidly ubiquitinated on lysine-156 and lysine-158 and degraded by proteasomes (Gong et al. 2006; Lee et al. 2006a; Lee et al. 2006b). Cellular stresses such as hypotonic shock and ER stress also activate SREBP via rapid turnover of Insig-1 (Lee and Ye 2004). The degradation of Insig1 In the ER is an essential determining step in release of immature SREBP-1 and its subsequent proteolytic activation in Golgi.

SUMMARY

The present application Is directed generally to the use of polypeptide and antibody inhibitors of ubiquitination of Insig-1, and to the use of compositions comprising the polypeptide or antibody inhibitors, to treat skin disorders associated with excess sebum production.

Human Insig-1 (EntrezGene ID: 3638) is targeted for degradation by ubiquitination on lysine-156 and lysine-158. Polypeptides of the disclosure comprise amino acid sequences derived from the ubiquitination site of human Insig-1, including amino acid residues lysine-156 and lysine-158 flanked by at least one N-terminal amino acid residue and one C-terminal amino acid residue. Upon application to a sebocyte, these polypeptides may compete with the native Insig-1 protein as a target for ubiquitination, thereby reducing, preventing, or inhibiting ubiquitination of Insig-1; leading to reduction, prevention, or inhibition of Insig-1 within the sebocyte and interfering with the SREBP-1 pathway. Polypeptides of the disclosure have been demonstrated to inhibit the production of sebaceous lipids from sebocytes, in both the presence and absence of linoleic acid and/or testosterone.

An embodiment of the disclosure is a composition for use to treat a skin disease or condition associated with overproduction of sebum, said composition comprising a polypeptide comprising an amino acid sequence as set forth in SEQ ID NO: 21 or a conservatively substituted amino acid sequence of SEQ ID NO: 21 that retains the lysine residues at amino add positions 2 and 4 of SEQ ID NO: 21 and a pharmaceutically or cosmetically acceptable carrier. In an embodiment, the pharmaceutically or cosmetically acceptable carrier is a topically acceptable carrier. In a further embodiment the composition additionally comprises a skin penetration enhancer.

In an embodiment, the polypeptide further comprises a linker.

In another embodiment, the composition comprises a cell penetrating peptide joined to the polypeptide. In an embodiment, the cell penetrating peptide is joined to the N-terminal end of the polypeptide, optionally by a linker. In another embodiment the cell penetrating polypeptide is joined to the C-terminal end of the polypeptide, optionally by a linker.

In an embodiment, the composition comprises a polypeptide comprising an amino acid sequence of any one of SEQ ID NOs: 1 to 20 or a conservatively substituted amino acid sequence of any one of SEQ ID NOs: 1 to 20.

In an embodiment, the polypeptide is up to 25 amino acids residues in length. In another embodiment, the polypeptide is up to 40 amino acids in length. In another embodiment, the polypeptide is up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 31, up to 32, up to 33, up to 34, up to 35, up to 36, up to 37, up to 38, up to 39, or up to 40 amino acids in length. In another embodiment, the polypeptide is between 5 and 21 amino acids in length. In another embodiment, the polypeptide is at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or greater than 25 amino adds in length.

In an embodiment, the polypeptide comprises an amino acid sequence of any one of SEQ ID NOs: 1, 7-12, 14, 15, and 18-21 flanked at the N and/or C terminus by one or more amino acids that are not native to the sequence flanking the N and/or C terminus of the corresponding portion of human Insig-1. In an embodiment, the polypeptide comprises an amino acid sequence of any one of SEQ ID NOs: 1, 7-12, 14, 15, and 18-21 flanked at the N and/or C terminus by at least one, two, or three amino acids that are not native to the sequence flanking the N and/or C terminus of the corresponding portion of human Insig-1.

In an embodiment, the polypeptide comprises an amino acid having at least 80% sequence identity to SEQ ID NO: 1 or SEQ ID NO: 2 or having at least 80% sequence identity to a conservatively substituted amino acid sequence of SEQ ID NO:1 or SEQ ID NO:2.

In an embodiment, the polypeptide comprises an amino acid sequence having at least 90% sequence identity to SEQ ID NO: 1 or SEQ ID NO: 2 or having at least 90% sequence identity to a conservatively substituted amino acid sequence of SEQ ID NO:1 or SEQ ID NO:2.

In an embodiment, the polypeptide comprises an amino acid sequence having at least 95% sequence identity to SEQ ID NO: 2 or having at least 95% sequence identity to a conservatively substituted amino acid sequence of SEQ ID NO:2.

In an embodiment, the polypeptide comprises an amino acid sequence having an amino acid sequence of SEQ ID NO: 1 or SEQ ID NO: 2 with a single non-conservative amino acid substitution, deletion, or insertion or having a conservatively substituted amino acid sequence of SEQ ID NO: 1 or SEQ ID NO: 2 with a single non-conservative amino acid substitution, deletion, or insertion, and the polypeptide is capable of inhibiting ubiquitination of Insig-1.

In an embodiment, the polypeptide comprises an amino acid sequence of SEQ ID NO: 1 or SEQ ID NO: 2 or a conservatively substituted amino acid sequence of SEQ ID NO: 1 or SEQ ID NO: 2.

In an embodiment, the polypeptide comprises an amino acid sequence of SEQ ID NO: 1 or SEQ ID NO: 2.

In an embodiment, the polypeptide has an amino acid sequence consisting of SEQ ID NO: 1 or SEQ ID NO: 2.

Another embodiment is a topical composition for use to treat a skin disease or condition associated with overproduction of sebum comprising a polypeptide of the disclosure.

A further embodiment is a composition for use to treat a skin disease or condition associated with overproduction of sebum, said composition comprising an antibody that binds to the ubiquitination site of human Insig-1. In an embodiment, the skin disease or condition is acne or seborrheic dermatitis. In another embodiment, the skin condition is acne.

In an embodiment, the antibody is specific for a polypeptide having an amino acid sequence as set forth in any one of SEQ ID NOs: 1 to 21. In another embodiment, the antibody is specific for a polypeptide having an amino acid sequence as set forth in SEQ ID NO: 1 or 2.

Yet another embodiment is a method of treating a skin condition associated with overproduction of sebum, the method comprising administering a polypeptide or antibody of the disclosure to a subject in need of treatment. In an embodiment the skin condition is acne or seborrheic dermatitis. In another embodiment the skin condition is acne. In an embodiment, the administration is topical administration.

A still further embodiment is use of a polypeptide or antibody of the disclosure to treat a skin condition associated with overproduction of sebum. In an embodiment the skin condition is acne or seborrheic dermatitis. In an embodiment the skin condition is acne.

Another embodiment is a method of altering lipid production by a sebocyte cell by administering to the cell a polypeptide or antibody of the disclosure. In an embodiment, the administration is in vitro administration. In an embodiment, the alteration is a reduction in lipid production relative to a control sebocyte cell.

In one aspect there is provided a method of treatment of a subject having or suspected of having a skin condition associated with overproduction of sebum, the method comprising administering to a subject a therapeutically effective amount of a compound capable of preventing or inhibiting ubiquitination of Insig-1. The compound may be a peptide. The compound may further comprise a protein transduction domain. The compound may be a polypeptide having an amino acid composition substantially similar to SEQ ID NO: 1 or SEQ ID NO: 2. The compound may be an antibody. The compound may be an antibody raised against or that binds to a polypeptide having an amino acid composition substantially similar to SEQ ID NO: 1 or SEQ ID NO: 2. The antibody may be an intracellular antibody. The skin condition may be acne.

In other aspects, there is provided a method for preventing, inhibiting or reducing SREBP-1 in a sebaceous lipid producing cell, the method comprising contacting the cell with a polypeptide having an amino acid composition substantially similar to SEQ ID NO: 1 or SEQ ID NO: 2. The sebaceous lipid producing cell may be a sebocyte.

In another aspect there is provided a method of prevention of a skin condition associated with SREBP-1 in a subject, the method comprising administering to a subject a therapeutically effective amount of a compound capable of preventing or inhibiting ubiquitination of Insig-1. The compound may be a peptide. The compound may further comprise a protein transduction domain. The compound may be a polypeptide having an amino acid composition substantially similar to SEQ ID NO: 1 or SEQ ID NO: 2. The compound may be an antibody. The compound may be an antibody raised against or that binds to a polypeptide having an amino acid composition substantially similar to SEQ ID NO: 1 or SEQ ID NO: 2. The antibody may be an intracellular antibody. The skin condition may be acne.

DETAILED DESCRIPTION

Figure 1A:
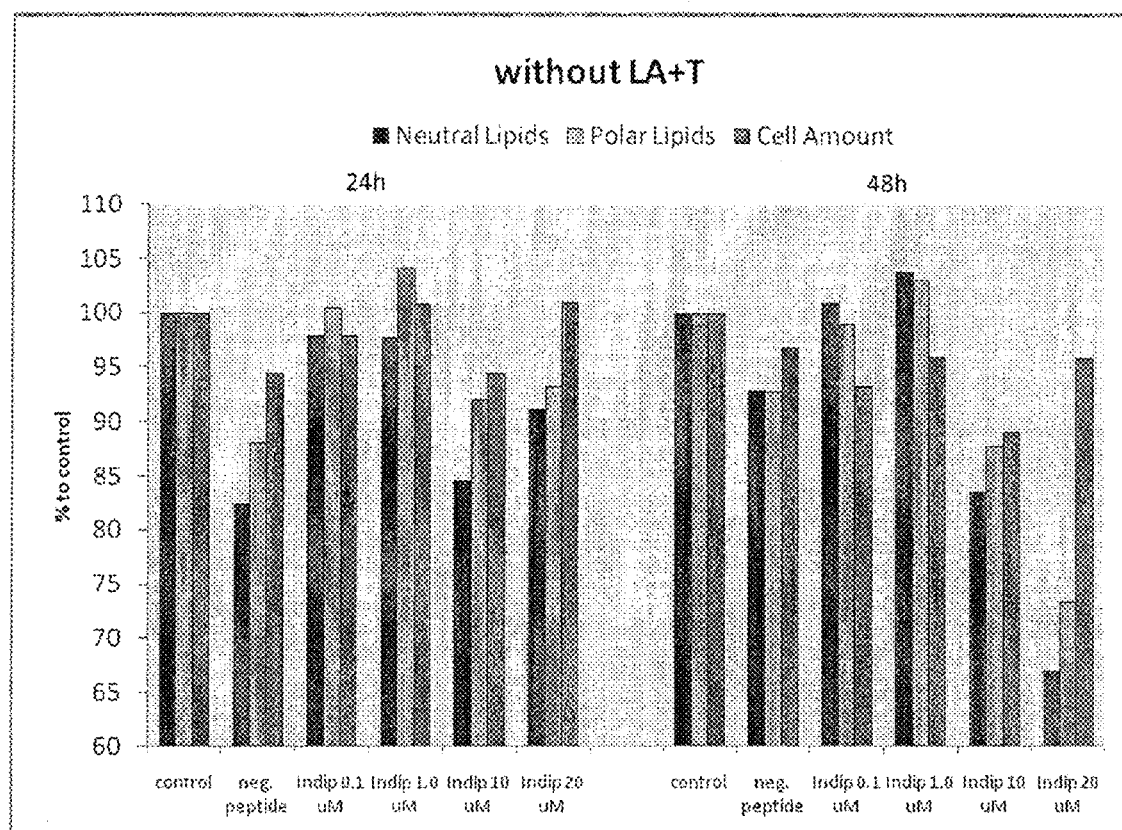
FIGS. 1A, 1B, and 1C. Effect of an INDIP peptide (SEQ ID NO: 2) on sebaceous lipid production. Increasing amounts of the INDIP peptide were applied to SZ95 sebocytes either in the absence (A) of linoleic acid and testosterone, or in the presence (B and C) of different amounts of linoleic acid and testosterone.

Any terms not directly defined herein shall be understood to have the meanings commonly associated with them as understood within the art. As employed throughout the specification, the following terms, unless otherwise indicated, shall be understood to have the following meanings.

As used herein "a", "an" and/or "the" Includes one and/or more than one.

As used herein the term "about" means than the value or range of values can be greater than or lesser than the stated value or range of values by 10%, but is not intended to limit any value or range of values to only this broader definition. Each value or range of values preceded by the term "about" Is also intended to encompass the stated absolute value or range of values.

As used herein the term "subject" refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a mouse or a rat.

The term "SCAP" refers to SREBP cleavage activating protein, which is encoded by the gene corresponding to EntrezGene ID: 22937. SREBP cleavage-activating protein (SCAP) is a regulatory protein that is required for the proteolytic cleavage of the sterol regulatory element binding protein (SREBP). SCAP is an integral membrane protein located in the endoplasmic reticulum (ER). One of the cytosolic regions of SCAP contains a hexapeptide amino acid sequence, MELADL, that functions to detect cellular cholesterol. When cholesterol is present, SCAP undergoes a conformational change that prevents it from activating SREBP and cholesterol synthesis does not occur. SCAP has 8 transmembrane domains and both the N-terminal and C-terminal face the cytoplasm. Also, it binds SREBP by a series of consecutive WD repeats on its C-terminus.

The term "SREBP1" refers to sterol regulatory element binding protein 1, which may alternately be referred to as SREBF-1 or SREBP-1. The gene which encodes this protein corresponds to EntrezGene ID: 6720. SREBPs belong to the basic-helix-loop-helix leucine zipper class of transcription factors. Unactivated SREBPs are attached to the endoplasmic reticulum membrane. In cells with low levels of sterols, SREBPs are cleaved to a water soluble N-terminal domain which is translocated to the nucleus. These activated SREBPs then bind to specific sterol regulatory element DNA sequences which upregulate the synthesis of enzymes involved in sterol biosynthesis. Sterols in turn inhibit the cleavage of SREBPs and therefore synthesis of additional sterols is reduced through a negative feedback loop, as described herein.

The term "Insig-1" refers to the protein product of insulin-induced gene 1 (EntrezGene ID: 3638). The polypeptide is 277 amino acids in length. This protein binds to the sterol-sensing domains of SREBP cleavage-activating protein (SCAP) and HMG CoA reductase, and is essential for the sterol-mediated trafficking of the two proteins. Alternatively spliced transcript variants encoding distinct isoforms have been observed. Degradation of Insig-1 by ubiquitin-mediated pathways is essential for SCAP/SREBP regulation, as described herein. Human Insig-1 is targeted for degradation by ubiquitination on lysine-156 and lysine-158. The present application provides various compositions and methods for modulating ubiquitination of Insig-1.

The terms "peptide", "polypeptide" and "protein" may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide. Examples of modifications to peptides may include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties*, 2$^{nd}$ ed., T. E. Creighton, W. H. Freeman and Company, New York, 1993 and Wold F, *Posttranslational Protein Modifications: Perspectives and Prospects*, pgs. 1-12 in *Posttransiational Covalent Modification of Proteins*, B. C. Johnson, ed., Academic Press, New York, 1983; Seifter et al., *Analysis for protein modifications and nonprotein cofactors, Meth. Enzymol.* (1990) 182: 626-646 and Rattan et al. (1992), *Protein Synthesis: Posttranslational Modifications and Aging,"* Ann NY Acad Sci 663: 48-62.

As used herein, the term "cell-penetrating peptide", also referred to as a "protein transduction domain", refers to a peptide that is capable of carrying a large macromolecule, such as a peptide, across a cellular membrane, for example as described in Nasrollahi et al (2012), Chem Biol Drug Des 80: 639-646. Cell penetrating peptides are relatively short (up to 30 amino acids in length), water soluble, cationic and/or amphipathic peptides that may be joined to polypeptides, for example through recombinant expression, covalent linkage, or peptide synthesis, to improve the ability of the polypeptide to pass through cell membranes. The cell penetrating peptide may be joined to either the N-terminal end of the polypeptide or the C-terminal end of the polypeptide, optionally by a linker. Cell penetrating peptides have also been shown to facilitate skin penetration. As used herein the term "cell penetrating peptide" is also intended to include skin penetrating peptides, for example as described in Menegatti et al (2016), Advanced Healthcare Materials, 5(5): 602-609 and Kumar et al (2015) Journal of Controlled Release 199:168-178. Cell penetrating and skin penetrating peptides are known in the art and include Penetratin, Tat, Transportan, MAP, KALA, P1, MPG, Pep-1, polyarginine, polylysine, hCT, SPACE, and TD-1.

As used herein the term "linker" is intended to include peptide linkers and chemical cross-linkers. Peptide linkers are relatively short amino acid sequences used to join one polypeptide sequence to another. Typically a peptide linker will be between about 1 to about 30 amino adds in length. The peptide linker may be a flexible linker having a glycine-rich sequence. For example, the linker may comprise a series of one to five, or more, glycine residues. Chemical cross-linkers for covalently joining polypeptides are well known in the art and include but are not limited to amine-to-amine crosslinkers, sulfhydryl-to-sulfhydryl crosslinkers, amine-to-sulfhydryl crosslinkers, in vivo crosslinking reagents, and carboxyl-to-amine crosslinkers.

A "substantially similar" amino acid sequence is an amino add sequence that differs from a reference sequence by one or more conservative substitutions, but which may, for example, be functionally homologous to another substantially similar sequence. It will be appreciated by a person of skill in the art the aspects of the individual amino acids in a peptide of the application that may be substituted.

Amino acid sequence similarity or identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, *J Mol. Biol.* 215: 403-410 and ALTSCHUL et al. (1997), *Nucleic Acids Res.* 25: 3389-3402.

Amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

Nomenclature used to describe the peptide compounds of the present application follows the conventional practice where the amino group is presented to the left and the carboxyl group to the right of each amino acid residue. In the sequences representing selected specific embodiments of the present application, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid, in accordance with the following Table 1:

TABLE 1

Nomenclature and abbreviations of the 20 standard L-amino acids commonly found in naturally occurring peptides.

| Full name | Three-letter abbreviation | One-letter abbreviation |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

The hydropathy index of an amino acid is a scale indicating the tendency of an amino acid to seek out an aqueous environment (negative value) or a hydrophobic environment (positive value) (KYTE & DOOLITTLE 1982. *J Mol Biol* 157:105-132). Hydropathy indices of the standard amino acids include alanine (1.8), arginine (−4.5), asparagine (−3.5), aspartic acid (−3.5), cysteine (2.5), glutamine (−3.5), glutamic acid (−3.5), glycine (−0.4), histidine (−3.2), isoleucine (4.5), leucine (3.8), lysine (−3.9), methionine (1.9), phenylalanine (2.8), proline (−1.6), serine (−0.8), threonine (−0.7), tryptophan (−0.9), tyrosine (−1.3), and valine (4.2). Amino acids with similar hydropathy indices may be substitutable for each other in a peptide.

Amino acids contained within the peptides described herein will be understood to be in the L- or D-configuration. In peptides and peptidomimetics of the present application, D-amino acids may be substitutable for L-amino acids. Amino acids contained within the peptides of the present application, and particularly at the carboxy- or amino-terminus, may be modified by methylation, amidation, acetylation or substitution with other chemical groups which may change the circulating half-life of the peptide without adversely affecting their biological activity. Additionally, a disulfide linkage may be present or absent in the peptides of the application.

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-imino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

The polypeptides of the present application may be in isolation, or may be linked to or in combination with tracer compounds, protein transduction domains or sequences, liposomes, carbohydrate carriers, polymeric carriers or other agents or excipients as will be apparent to one of skill in the art. In an alternate embodiment, such peptides may comprise a medicament, wherein such peptides may be present in a pharmacologically effective amount.

Conservative substitutions: It will be understood by one skilled in the art that conservative substitutions may be made in the amino acid sequence of a polypeptide without disrupting the three-dimensional structure or function of the polypeptide. Accordingly, the present application includes polypeptides comprising conservatively substituted amino acid sequences of SEQ ID NO:1 and SEQ ID NO: 2. Conservative substitutions are accomplished by the skilled artisan by substituting amino acids with similar hydrophobicity, polarity, and R chain length for one another. Additionally, by comparing aligned sequences of homologous proteins from different species, conservative substitutions may be identified by locating amino acid residues that have been mutated between species without altering the basic functions of the encoded proteins. Table 2 provides an exemplary list of conservative substitutions.

TABLE 2

Conservative Amino Acid Substitutions

| Type of Amino Acid | Substitutable Amino Acids |
| --- | --- |
| Hydrophilic | Ala, Pro, Gly, Glu, Asp, Gln, Asn, Ser, |
| Sulphydryl | Cys |
| Aliphatic | Val, Ile, Leu, Met |
| Basic | Lys, Arg, His |
| Aromatic | Phe, Tyr, Trp |

The term "medicament" as used herein, a "medicament" refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term "pharmaceutically acceptable excipient" may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

The term "skin penetration enhancer" may include any and all skin penetration enhancers that are physiologically compatible. Examples of skin penetration enhancers include alcohols, amides, esters, ether alcohols, fatty adds, glycols, pyrrolidones, sulphoxides, surfactants, and terpenes. Use of such skin penetration enhancers for the formulation of topical delivery systems is known in the art.

As used herein, the term "skin disorder associated with overproduction of sebum" includes skin conditions believed to be caused or exacerbated by excessive sebum production by sebaceous glands. Sebum is produced by the sebaceous glands and is composed of keratin, fat, and cellular debris. Skin disorders associated with overproduction of sebum include acne and seborrhea; including seborrheic dermatitis (cradle cap, dandruff), seborrhea congestivea, seborrheic blepharitis, and seborrheic keratosis.

The term "treatment or treating" as used herein means an approach for obtaining beneficial or desired results, including clinical results. Treatment includes therapeutic treatment and prophylactic treatment. Beneficial or desired clinical results can include, but are not limited to, alleviation or amelioration of one or more symptoms or conditions, diminishment of extent of disease, stabilized (i.e. not worsening) state of disease, delay or slowing of disease progression, amelioration or palliation of the disease state, and, remission (whether partial or total), whether detectable or undetectable. The term "treatment or treating" In some embodiments means preventing disease at a subclinical stage.

The term a "therapeutically effective amount", "effective amount" or a "sufficient amount" of a composition of the present disclosure is a quantity sufficient to, when administered to the subject, including a mammal, for example a human, effect beneficial or desired results, including clinical results, and, as such, an "effective amount" or synonym thereto depends upon the context in which it is being applied. In the context of disease, therapeutically effective amounts of the agents are used to treat, modulate, attenuate, reverse, or affect disease, condition or disorder, such as the skin disorder associated with overproduction of sebum. An "effective amount" is intended to mean that amount of a composition that is sufficient to treat, prevent or inhibit such disorders, conditions or diseases. The amount of a given agent that will correspond to such an amount will vary depending upon various factors, such as the given agent, the pharmaceutical formulation, the route of administration, the type of condition, disease or disorder, the identity of the subject or host being treated, and the like, but can nevertheless be routinely determined by one skilled in the art. As defined herein, a therapeutically effective amount of an agent may be readily determined by one of ordinary skill by routine methods known in the art.

Moreover, a "treatment" or "prevention" regime of a subject with a therapeutically effective amount of an agent may consist of a single administration, or alternatively comprise a series of applications. For example, the agent may be administered at least once a week. However, in another embodiment, the agent may be administered to the subject from about one time per week to about twice daily for a given treatment. The length of the treatment period depends on a variety of factors, such as the severity of the disease, the age of the subject, the concentration and the activity of the agent, or a combination thereof. It will also be appreciated that the effective dosage of the agent used for the treatment or prophylaxis may increase or decrease over the course of a particular treatment or prophylaxis regime. Changes in dosage may result and become apparent by standard diagnostic assays known in the art. In some instances, chronic administration may be required.

The term "administering" Is defined as any conventional route for administering an agent to a subject for use, for example, in treating a skin condition, disease or disorder, as is known to one skilled in the art. This may include, for example, topical administration. In other embodiments this may include parenteral (i.e. subcutaneous, intradermal, intramuscular, intravenous, etc.), oral, sublingual, or mucosal administration and the like. The dose of the agent may vary according to factors such as the severity of the skin condition and the health, age, weight and/or sex of the subject. The dosage regime may be adjusted to provide the optimum dose. One skilled in the art will appreciate that the dosage regime can be determined and/or optimized without undue experimentation.

As used herein "altering lipid production" of a sebocyte cell includes a change in lipid production by the sebocyte cell as compared to a control sebocyte cell to which a polypeptide or antibody of the disclosure has not been administered. The change in lipid production may, for example, be a change in the rate of lipid production, the amount of lipid production, or a change in the lipid profile produced by the cell. In some instances, the change will be a reduction in the rate and/or amount of lipid produced by the sebocyte cell.

Administering a composition to a cell includes in vivo, ex vivo and in vitro administration.

The polypeptides and antibodies of the present disclosure may be administered as a sterile aqueous solution, or may be administered in a fat-soluble excipient, or in another solution, suspension, patch, tablet or paste format as is appropriate. A composition of the disclosure may be formulated for administration by inhalation. For instance, a polypeptide may be combined with an excipient to allow dispersion in an aerosol. Examples of inhalation formulations will be known to those skilled in the art. Other agents may be included in combination with the polypeptides of the present disclosure to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

Polypeptides of the disclosure may be included in a cosmetic composition. For example, polypeptides of the disclosure may be included in cosmetic products such as beauty masks, make-up, cosmetic patches, and creams or lotions.

The term "pharmaceutically acceptable" means compatible with the treatment of humans and animals.

The term "cosmetically acceptable" means compatible with cosmetic application to humans and animal.

Delivery of bioactive molecules such as polypeptides, to a cell or cells in a reasonably efficient manner may require more than just applying the naked peptide onto the cell, or administering the naked peptide into the patient or test subject. Agents that enable delivery of bioactive molecules into cells in a suitable manner so as to provide an effective amount, such as a pharmacologically effective amount are known in the art, and are described in, for example, DIETZ at al 2004. *Mol Cell. Neurosci* 27:85-131. Examples of such agents include liposomes, antibodies or receptor ligands that may be coupled to the bioactive molecule, viral vectors, and protein transduction domains (PTD). Examples of PTDs Include Antennapedia homeodomain (PEREZ et al 1992 *J. Cell Sci* 102:717-722), transportan (POOGA et al 1998 *FASEB J* 12: 67-77), the translocation domains of diphtheria toxin (STENMARK et al 1991 *J Cell Biol* 113:1025-1032; WIEDLOCHA et al 1994 *Cell* 76:1039-1051), anthrax toxin (BALLARD at al 1998 *Infect. Immun* 66:615-619; BLANKE et al 1996 *Proc Natl Acad Sci* 93: 8437-8442) and *Pseudomonas* exotoxin A (PRIOR et al 1992 *Biochemistry* 31:3555-3559), protegrin derivatives such as dermaseptin S4 (HARITON-GAZAL et al 2002 *Biochemistry* 41:9208-9214), HSV-1 VP22 (DILBER et al 1999 *Gene Ther.* 6:12-21), PEP-1 (MORRIS et al 2001 *Nature Biotechnol* 19:1173-1176), basic peptides such as poly-L and poly-D-lysine (WOLFERT et al 1996 *Gene Ther.* 3:269-273; RYSER at al 1980 *Cancer* 45:1207-1211; SHEN et al 1978 *Proc Natl Acad Sci* 75:1872-1876), HSP70 (FUJIHARA et al 1999 *EMBO J* 18:411-419) and HIV-TAT (DEMARCHI et al 1996 *J Virol* 70:4427-4437). Other examples and related details of such protein transduction domains are described in DIETZ, supra and references therein. In an embodiment, a composition of the disclosure may comprise a delivery agent.

The term "antibody" as used herein refers to immune system proteins, also called immunoglobulins, produced in response to foreign substances (antigens). Antibodies typically contain two heavy chains and two light chains, which are joined. Variability in the structure of these chains provides antigen specificity—ie. allows individual antibodies to recognize specific antigens. The term antibody may include polyclonal and monoclonal antibodies, chimeric, single chain, or humanized antibodies, as well as Fab or F(ab)² fragments, including the products of an Fab or other immunoglobulin expression library. Methods of making such antibodies or fragments are known in the art and may be found in, for example HARLOW, E and LANE D. Antibodies: A Laboratory Manual. 1988. Cold Spring Harbor Laboratory Press.

Antibodies according to some embodiments may also be intracellular antibodies, sometimes referred to as intrabodies. Methods for designing, making and/or using such antibodies have been described in the art, for Instance Lecerf et al. 2001; Hudson and Souriau 2003. Selection or identification of specific peptides for use as epitopes for production of antibodies that differentiate between proteins, or isoforms of proteins may be made using sequence comparisons—one of skill in the art will be able to identify suitable peptide or protein sequences that may be useful for producing antibodies with the desired selectivities. Polyclonal antibodies are antibodies that are derived from different B-cell lines. They are a mixture of immunoglobulin molecules secreted against a specific antigen, each recognizing a different epitope. These antibodies are typically produced by immunization of a suitable mammal, such as a mouse, rabbit or goat. Larger mammals are often preferred as the amount of serum that can be collected is greater. An antigen is injected into the mammal. This induces the B-lymphocytes to produce IgG immunoglobulins specific for the antigen. This IgG is purified from the mammal's serum. By contrast, monoclonal antibodies are derived from a single cell line.

Adjuvants may be used to improve or enhance an immune response to antigens. In certain embodiments, there are provided antibodies raised against or that bind to a polypeptide having an amino acid composition substantially similar to SEQ ID NO: 1. There are also provide methods for inhibiting or preventing ubiquitination of Insig-1 utilizing such antibodies. There are also provided methods for treating or preventing a number of diseases in a subject using such antibodies.

The polypeptides and compositions of the disclosure may be capable of inhibiting ubiquitination of Insig-1, and thereby inhibiting SREBP-1. Examples of such polypeptides include polypeptides comprising the amino add sequences set forth in Table 3, as well as conservatively substituted derivatives of the amino acid sequences set forth in Table 3. Examples of such polypeptides also include polypeptides having single amino acid substitutions (conservative or non-conservative), deletions, or insertions of the amino acid sequences set forth in Table 3, provided that the resulting polypeptides retain the ability to inhibit ubiquitination of Insig-1. Examples of such polypeptides additionally include those described in WO2009121176A1, which is hereby incorporated by reference.

TABLE 3

| Sequence Listing | |
|---|---|
| SEQ ID NO: | SEQUENCE |
| 1 | GEPHKFKREW |
| 2 | YGRKKRRQRRRGEPHKFKREW |
| 3 | GGEPHKFKREW |
| 4 | GGGEPHKFKREW |
| 5 | GGGGEPHKFKREW |

TABLE 3-continued

Sequence Listing

| SEQ ID NO: | SEQUENCE |
|---|---|
| 6 | GGGGGEPHKFKREW |
| 7 | EPHKFKREW |
| 8 | GEPHKFKRE |
| 9 | EPHKFKRE |
| 10 | GEPHKFKRE |
| 11 | EPHKFKRE |
| 12 | PHKFKRE |
| 13 | PHKFKR |
| 14 | PHKFKK |
| 15 | DPHKFKREW |
| 16 | EPHKFKREF |
| 17 | DPHKFKREF |
| 18 | EPHKFKRDW |
| 19 | EPHKFKRD |
| 20 | PHKFKRD |
| 21 | HKFKR |

Polypeptides of the disclosure may be capable of preventing or inhibiting ubiquitination of Insig-1, and thereby inhibiting SREBP-1. An example of such a polypeptide is illustrated below in working Example 1. Peptides derived from a peptide having substantial similarity to the ubiquitination region of the Insig-1 protein are referred to herein as INDIP peptides. The term "INDIP peptide" Includes polypeptides comprising SEQ ID NOs 1 to 21 and polypeptides comprising conservatively substituted SEQ ID NOs 1 to 21. Generally speaking, INDIP peptides comprise a short fragment of the Insig-1 ubiquitination region and may be attached to a protein transduction domain such as the TAT protein transduction domain to produce a PTD-fused Insig-1 ubiquitination region peptide (for example, see SEQ ID NO: 2). INDIP peptides have been previously described (WO2009121176A1).

An embodiment of the disclosure is a composition for use to treat a skin disease or condition associated with overproduction of sebum, said composition comprising a polypeptide comprising an amino acid sequence as set forth in SEQ ID NO: 21 or a conservatively substituted amino acid sequence of SEQ ID NO: 21 that retains the lysine residues at amino acid positions 2 and 4 of SEQ ID NO: 21 and a pharmaceutically or cosmetically acceptable carrier. In an embodiment, the pharmaceutically or cosmetically acceptable carrier is a topically acceptable carrier. In a further embodiment the composition additionally comprises a skin penetration enhancer.

In an embodiment, the polypeptide further comprises a linker.

In another embodiment, the composition comprises a cell penetrating peptide joined to the polypeptide. In an embodiment, the cell penetrating peptide is joined to the N-terminal end of the polypeptide, optionally by a linker. In another embodiment the cell penetrating polypeptide is joined to the C-terminal end of the polypeptide, optionally by a linker.

In an embodiment, the composition comprises a polypeptide comprising an amino acid sequence of any one of SEQ ID NOs: 1 to 20 or a conservatively substituted amino acid sequence of any one of SEQ ID NOs: 1 to 20.

In an embodiment, the polypeptide is up to 25 amino acids residues in length. In another embodiment, the polypeptide is up to 40 amino acids in length. In another embodiment, the polypeptide is up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 31, up to 32, up to 33, up to 34, up to 35, up to 36, up to 37, up to 38, up to 39, or up to 40 amino acids in length. In another embodiment, the polypeptide is between 5 and 21 amino acids in length. In another embodiment, the polypeptide is at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or greater than 25 amino acids in length.

In an embodiment, the polypeptide comprises an amino acid sequence of any one of SEQ ID NOs: 1, 7-12, 14, 15, and 18-21 flanked at the N and/or C terminus by one or more amino acids that are not native to the sequence flanking the N and/or C terminus of the corresponding portion of human Insig-1. In an embodiment, the polypeptide comprises an amino acid sequence of any one of SEQ ID NOs: 1, 7-12, 14, 15, and 18-21 flanked at the N and/or C terminus by at least one, two, or three amino acids that are not native to the sequence flanking the N and/or C terminus of the corresponding portion of human Insig-1.

In an embodiment, the polypeptide comprises an amino acid having at least 80% sequence identity to SEQ ID NO: 1 or SEQ ID NO: 2 or having at least 80% sequence identity to a conservatively substituted amino acid sequence of SEQ ID NO:1 or SEQ ID NO:2.

In an embodiment, the polypeptide comprises an amino acid sequence having at least 90% sequence identity to SEQ ID NO: 1 or SEQ ID NO: 2 or having at least 90% sequence identity to a conservatively substituted amino acid sequence of SEQ ID NO:1 or SEQ ID NO:2.

In an embodiment, the polypeptide comprises an amino acid sequence having at least 95% sequence identity to SEQ ID NO: 2 or having at least 95% sequence identity to a conservatively substituted amino acid sequence of SEQ ID NO:2.

In an embodiment, the polypeptide comprises an amino acid sequence having an amino acid sequence of SEQ ID NO: 1 or SEQ ID NO: 2 with a single non-conservative amino acid substitution, deletion, or insertion or having a conservatively substituted amino acid sequence of SEQ ID NO: 1 or SEQ ID NO: 2 with a single non-conservative amino acid substitution, deletion, or insertion, and the polypeptide is capable of inhibiting ubiquitination of Insig-1.

In an embodiment, the polypeptide comprises an amino acid sequence of SEQ ID NO: 1 or SEQ ID NO: 2 or a conservatively substituted amino acid sequence of SEQ ID NO: 1 or SEQ ID NO: 2.

In an embodiment, the polypeptide comprises an amino acid sequence of SEQ ID NO: 1 or SEQ ID NO: 2.

In an embodiment, the polypeptide has an amino acid sequence consisting of SEQ ID NO: 1 or SEQ ID NO: 2.

Another embodiment is a topical composition for use to treat a skin disease or condition associated with overproduction of sebum comprising a polypeptide of the disclosure.

A further embodiment is a composition for use to treat a skin disease or condition associated with overproduction of sebum, said composition comprising an antibody that binds to the ubiquitination site of human Insig-1. In an embodiment, the skin disease or condition is acne or seborrheic dermatitis. In another embodiment, the skin condition is acne.

In an embodiment, the antibody is specific for a polypeptide having an amino acid sequence as set forth in any one of SEQ ID NOs: 1 to 21. In another embodiment, the antibody is specific for a polypeptide having an amino acid sequence as set forth in SEQ ID NO: 1 or 2.

Yet another embodiment is a method of treating a skin condition associated with overproduction of sebum, the method comprising administering a polypeptide or antibody of the disclosure to a subject in need of treatment. In an embodiment the skin condition is acne or seborrheic dermatitis. In another embodiment the skin condition is acne. In an embodiment, the administration is topical administration.

A still further embodiment is use of a polypeptide or antibody of the disclosure to treat a skin condition associated with overproduction of sebum. In an embodiment the skin condition is acne or seborrheic dermatitis. In an embodiment the skin condition is acne.

Another embodiment is a method of altering lipid production by a sebocyte cell by administering to the cell a polypeptide or antibody of the disclosure. In an embodiment, the administration is in vitro administration. In an embodiment, the alteration is a reduction in lipid production relative to a control sebocyte cell.

In another embodiment, there is provided a method of treatment of a subject having or suspected of having a skin condition associated with SREBP-1, the method comprising administering to a subject a therapeutically effective amount of a compound capable of preventing or inhibiting ubiquitination of Insig-1. The compound may be a peptide. The compound may further comprise a protein transduction domain. The compound may be a polypeptide having an amino acid composition substantially similar to SEQ ID NO: 1 or SEQ ID NO: 2. The compound may be an antibody. The compound may be an antibody raised against or that binds to a polypeptide having an amino acid composition substantially similar to SEQ ID NO: 1 or SEQ ID NO: 2. The antibody may be an intracellular antibody. The skin condition may be acne.

In another aspect there is provided a method of prevention of a skin condition associated with SREBP-1 in a subject, the method comprising administering to a subject a therapeutically effective amount of a compound capable of preventing or inhibiting ubiquitination of Insig-1. The compound may be a peptide. The compound may further comprise a protein transduction domain. The compound may be a polypeptide having an amino acid composition substantially similar to SEQ ID NO: 1 or SEQ ID NO: 2. The compound may be an antibody. The compound may be an antibody raised against or that binds to a polypeptide having an amino acid composition substantially similar to SEQ ID NO: 1 or SEQ ID NO: 2. The antibody may be an intracellular antibody. The skin condition may be acne.

The following non-limiting example is illustrative of the present disclosure:

Example 1—Application of an INDIP Peptide (SEQ ID NO: 2) to SZ95 Sebocytes In Vitro Causes Significant Reduction in Lipid Production SZ95 is an immortalized human sebocyte cell line that is widely used as an in vitro human sebocyte model. Cultured SZ95 sebocytes have been shown to retain major characteristics of normal human sebocytes, including the expression of sebaceous gland protein markers and expected biological responses to androgens and retinoids (Zouboulis C C, Seltmann H, Neitzel H, Orfanos C E. Establishment and characterization of an immortalized human sebaceous gland cell line (SZ95) J Invest Dermatol. 1999; 113:1011-1020 and Wróbel A, Seltmann H, Fimmel S, Müller-Decker K, Tsukada M, Bogdano V B, et al. Differentiation and apoptosis in human immortalized sebocytes. J Invest Dermatol. 2003; 120:175-181).

Methods

Cell Cultures.

Immortalized human facial SZ95 sebocytes, which have been shown to conserve the major characteristics of normal sebocytes [Zouboulis, Ch. C., Seltmann, H., Neitzel, H. & Orfanos, C. E. (1999) J. Invest. Dermatol. 113, 1011-1020], were maintained in Sebomed Basal Medium (Biochrom, Berlin) supplemented with 5 ng/ml human epidermal growth factor (Sigma), 10% heat inactivated FCS (Biochrom GmbH, Berlin, Germany), 50 ug/ml gentamicin (GIBCO/BRL), and 1 mM Ca2+, in a humidified atmosphere of 5% CO2 at 37° C. Shortly before the experiments were performed, BSA-medium [constituted of Sebomed Basal Medium supplemented with 1 mg/ml fatty acid-free BSA (Boehringer Mannheim), 1 mM Ca2+, and 10-6 M linoleic acid (Sigma)] or Sebomed Complete Medium (Biochrom) was added to the cells. The SZ95 human sebocytes used for the experiments were between passages 31 and 35. The cells were subcultured at 60-70% confluence. The cultures were maintained at 37° C. in a humidified 5% CO2 incubator and the medium was replaced every 2-3 days.

Detection of Lipids.

The cells were cultured in 96-well tissue culture plates at a density of 2,000 cells per well for 2 days. The wells were then washed with PBS, and Sebomed Complete Medium was added. After 2 days, the medium was harvested, and fresh medium without or with INDIP peptide (SEQ ID NO: 2) at a concentration of 0, 0.1, 1, 10, or 20 µM in the presence and absence of Linoleic acid ($5 \times 10^{-5}$ and $10^{-4}$ M) and Testosterone ($2 \times 10^{-8}$ M) was given to the cells. The supernatants were harvested 24 or 48 h later; the wells were washed twice with PBS, and 100 µl of a 10 µg/ml nile red solution in PBS was added to each well. 10 uM of scrambled INDIP peptide (i.e. a scrambled version of SEQ ID NO: 2) was used as the negative control peptide. The plates were then incubated at 37° C. for 30 min, and the released fluorescence was read on a Molecular Devices SPECTRAmax Gemini spectrofluorometer. The results are presented as percentages of the absolute fluorescence units in comparison with the controls, using 485 nm excitation and 565 nm emission filters for neutral lipids and 540 nm excitation and 620 nm emission filters for polar lipids. Experiments were performed in triplicate, with 10 wells evaluated for each data point in each experiment.

Proliferation and Cell Number Analysis.

Cells were cultured in 96-well tissue culture plates at a density of 2,000 cells per well for 2 days. The wells were then washed with PBS, and BSA-medium with or without active compounds was added. Cell proliferation was conducted using the 4-methylumbelliferyl heptanoate fluorescence assay and measured automatically, as previously described [Zouboulis, Ch. C., Garbe, C., Krasagakis, K., Kruger, S., Schroder, K. & Orfanos, C. E. (1991) Melanoma Res. 1, 91-95.]. Briefly, after removing the media, the cells were washed twice with PBS, and 100 µl of a 100 µg/ml 4-methylumbelliferyl heptanoate solution in PBS was added to each well. The plates were then incubated at 37° C. for 30 min, and the released fluorescence, which is representative for cell numbers, was read on a Molecular Devices SPECTRAmax Gemini spectrofluorometer using 355 nm excitation and 460 nm emission filters. Relative cell numbers were plotted as "Cell Amount". Experiments were performed in quadruplicate, with 10 wells evaluated for each data point in each experiment.

Results

Figure 1B:
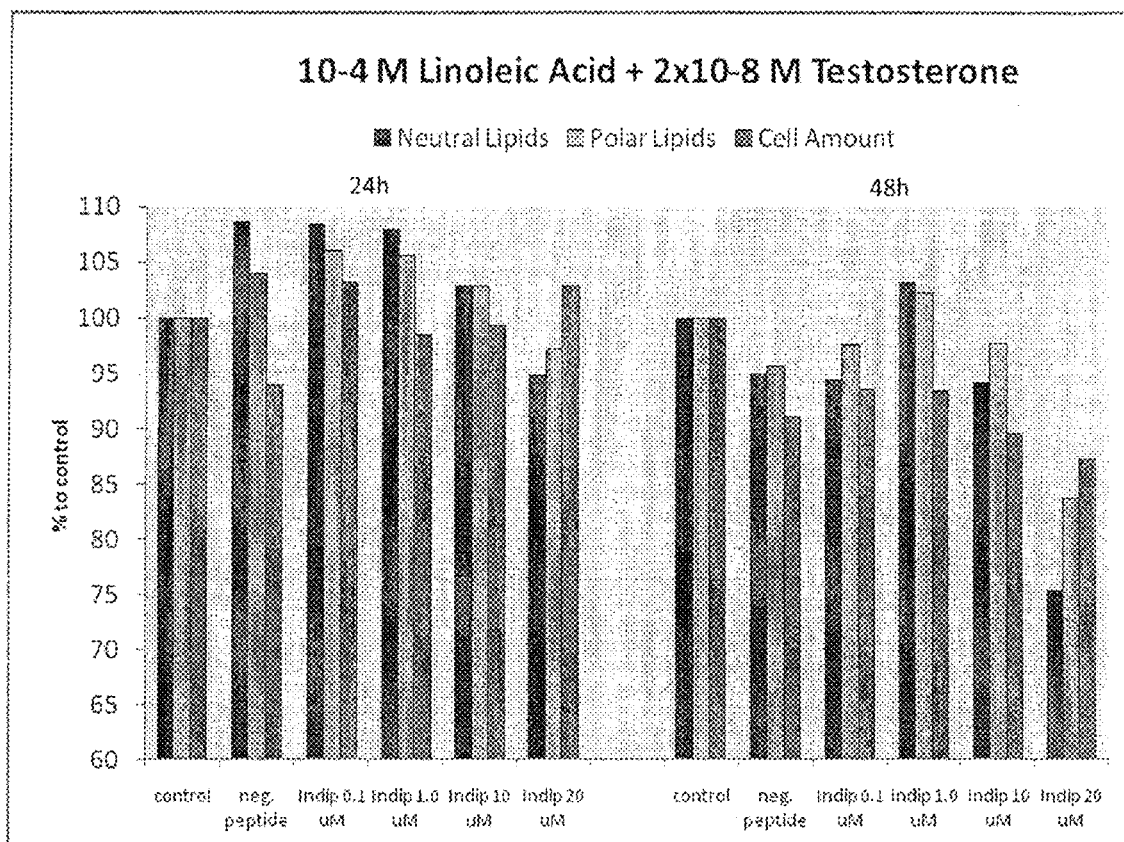
Figure 1C:
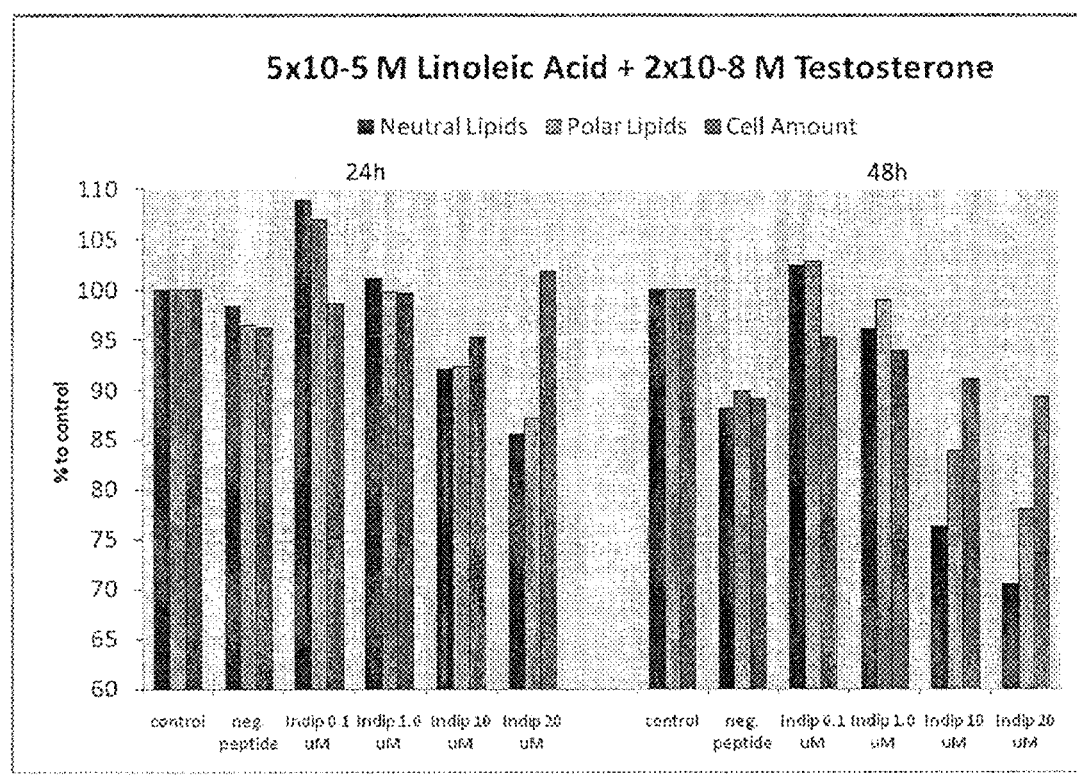

FIGS. 1A, 1B, and 1C show the results of addition of an INDIP peptide (SEQ ID NO: 2) to in vitro cell cultures of SZ95 sebocytes. FIG. 1A shows the results of application of the INDIP peptide without the addition of stimulants linoleic acid and testosterone, while FIGS. 1B and 1C show the results of application of increasing concentrations of the INDIP peptide in the presence of different concentrations of linoleic acid and testosterone. At a 20 µM, and occasionally at a 10 µM concentration of the INDIP peptide, the production of neutral (sebaceous) lipids was significantly reduced over time, with a greater effect seen as time progressed (24 vs 48 hours). These results were seen either in the absence or in the presence of linoleic acid and testosterone. The concomitant reduction of polar lipids indicates a parallel reduction of membrane synthesis, i.e. a reduction of the synthetic activity of the cells. This indicates that the INDIP peptide (SEQ ID NO: 2) is able to reduce sebaceous differentiation in all conditions tested, with and without the stimulating effect of the combined iinoleic acid and testosterone.

While the present disclosure has been described with reference to specific examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Flury, I., R. Garza, et al. (2005). "INSIG: a broadly conserved transmembrane chaperone for sterol-sensing domain proteins." Embo J 24(22): 3917-26.

Goldstein, J. L., R. A. DeBose-Boyd, et al. (2006). "Protein sensors for membrane sterols." Cell 124(1): 35-46.

Gong, Y., J. N. Lee, et al. (2006). "Sterol-regulated ubiquitination and degradation of Insig-1 creates a convergent mechanism for feedback control of cholesterol synthesis and uptake." Cell Metab 3(1): 15-24.

Hudson, P. J. and C. Sourau (2003). "Engineered antibodies." Nat Med 9(1): 129-34.

Lecerf, J. M., T. L. Shirley, et al. (2001). "Human single-chain Fv intrabodies counteract in situ huntingtin aggregation in cellular models of Huntington's disease." Proc Natl Acad Sci USA 98(8): 4764-9.

Lee, J. N., Y. Gong, et al. (2006a). "Proteasomal degradation of ubiquitinated Insig proteins is determined by serine residues flanking ubiquitinated lysines." Proc Natl Acad Sci USA 103(13): 4958-63.

Lee, J. N., B. Song, et al. (2006b). "Sterol-regulated degradation of Insig-1 mediated by the membrane-bound ubiquitin ligase gp78." J Biol Chem 281(51): 39308-15.

Lee, J. N. and J. Ye (2004). "Proteolytic activation of sterol regulatory element-binding protein induced by cellular stress through depletion of Insig-1." J Biol Chem 279 (43): 45257-65.

Nohturfft, A., M. S. Brown, et al. (1998). "Topology of SREBP cleavage-activating protein, a polytopic membrane protein with a sterol-sensing domain." J Biol Chem 273(27): 17243-50.

Sun, L. P., L. Li, et al. (2005). "Insig required for sterol-mediated inhibition of Scap/SREBP binding to COPII proteins in vitro." J Biol Chem 280(28): 26483-90.

Wróbel A, Seltmann H, Fimmel S, Müller-Decker K, Tsukada M, Bogdano V B, et al. Differentiation and apoptosis in human immortalized sebocytes. J Invest Dermatol. 2003; 120:175-181

Yang, T., P. J. Espenshade, et al. (2002). "Crucial step in cholesterol homeostasis: sterols promote binding of SCAP to INSIG-1, a membrane protein that facilitates retention of SREBPs in ER." Cell 110(4): 489-500.

Zouboulis, Ch. C., Garbe, C., Krasagakis, K., Kruger, S., Schroder, K. & Orfanos, C. E. (1991) Melanoma Res. 1, 91-95.

Zouboulis, Ch. C., Seltmann, H., Neitzel, H. & Orfanos, C. E. (1999) J. Invest. Dermatol. 113, 1011-1020.

What is claimed is:

1. A method of reducing overproduction of sebum associated with acne or seborrhea comprising administering an effective amount of a polypeptide comprising (a) the amino acid sequence as set forth in SEQ ID NO: 21; and (b) a cell penetrating peptide or a skin penetrating peptide joined to the amino acid sequence as set forth in SEQ ID NO: 21 to a subject in need of treatment for acne or seborrhea.

2. The method of claim 1, wherein the administration is topical administration.

3. The method of claim 1, wherein the skin condition is seborrheic dermatitis.

4. The method of claim 1, wherein the skin condition is acne.

5. The method of claim 1, wherein the polypeptide further comprises a linker connecting the cell penetrating peptide or the skin penetrating peptide to the amino acid sequence as set forth in SEQ ID NO:21.

6. The method of claim 1, wherein the polypeptide comprises an amino acid sequence having at least 90% sequence identity to SEQ ID NO: 1 or SEQ ID NO: 2.

7. The method of claim 1, wherein the polypeptide comprises an amino acid sequence having at least 95% sequence identity to SEQ ID NO:2.

8. The method of claim 1, wherein the polypeptide comprises the amino acid sequence of (a) SEQ ID NO: 1 and (b) the cell penetrating peptide or the skin penetrating peptide joined to the amino acid sequence of SEQ ID NO: 1.

9. The method of claim 1, wherein the polypeptide comprises the amino acid sequence of SEQ ID NO: 2.

10. A method of reducing overproduction of sebum associated with acne or seborrhea comprising administering an effective amount of a polypeptide to a subject in need of treatment for acne or seborrhea, said polypeptide comprising an amino acid sequence having the amino acid sequence of (a) SEQ ID NO: 2 or (b) (i) SEQ ID NO: 1 and (ii) a cell penetrating peptide or a skin penetrating peptide joined to the amino acid sequence of SEQ ID NO: 1.

* * * * *